(12) United States Patent
Kulkarni et al.

(10) Patent No.: US 11,781,426 B2
(45) Date of Patent: Oct. 10, 2023

(54) IDENTIFYING A LINE OF COHERENT RADIATION IN A CAPTURED IMAGE OF ILLUMINATED DOWNHOLE PARTICLES

(71) Applicant: Halliburton Energy Services, Inc., Houston, TX (US)

(72) Inventors: Abhijit Kulkarni, Houston, TX (US); Prashant Shekhar, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 43 days.

(21) Appl. No.: 16/428,458

(22) Filed: May 31, 2019

(65) Prior Publication Data

US 2019/0368347 A1 Dec. 5, 2019

Related U.S. Application Data

(60) Provisional application No. 62/680,675, filed on Jun. 5, 2018.

(51) Int. Cl.
*G06V 10/00* (2022.01)
*E21B 49/00* (2006.01)
(Continued)

(52) U.S. Cl.
CPC .......... *E21B 49/005* (2013.01); *E21B 21/065* (2013.01); *E21B 43/26* (2013.01);
(Continued)

(58) Field of Classification Search
CPC ... G06T 7/13; G06T 7/90; G06T 2207/30181; E21B 47/124; E21B 47/08; E21B 49/005;
(Continued)

(56) References Cited

U.S. PATENT DOCUMENTS 4,736,297 A 4/1988 LeJeune
4,739,655 A 4/1988 Greer et al.
(Continued)

FOREIGN PATENT DOCUMENTS

GB 2583843 5/2022
GB 2587138 1/2023
(Continued)

OTHER PUBLICATIONS

PCT Application Serial No. PCT/US2019/032967, International Search Report, dated Aug. 23, 2019, 3 pages.
(Continued)

*Primary Examiner* — Amir Alavi
*Assistant Examiner* — Nay A Maung
(74) *Attorney, Agent, or Firm* — DELIZIO, PEACOCK, LEWIN & GUERRA

(57) ABSTRACT

A line of coherent radiation is projected on a bed on which one or more particles is located, the one or more particles flowing produced as a result of a downhole operation in the borehole. An image of the bed is captured wherein one or more particles on the bed deflect the line of coherent radiation. One or more image edges is detected based on the captured image. A subset of the one or more image edges is identified as corresponding to edges of the one or more particles, based in part on changes in intensity of the captured image. Information about the one or more particles, including information about of size, shape and volume, can be determined from the one or more image edges corresponding to the edges of the one or more particles.

18 Claims, 9 Drawing Sheets

(51) Int. Cl.
*G06T 7/13* (2017.01)
*G06T 7/90* (2017.01)
*E21B 21/06* (2006.01)
*E21B 43/26* (2006.01)
*G01N 33/24* (2006.01)

(52) U.S. Cl.
CPC ............... *G01N 33/24* (2013.01); *G06T 7/13* (2017.01); *G06T 7/90* (2017.01); *G06T 2207/30181* (2013.01)

(58) Field of Classification Search
CPC ....... E21B 21/065; E21B 43/26; G01N 33/24; G01V 3/24
See application file for complete search history.

(56) References Cited

U.S. PATENT DOCUMENTS

| | | | |
|---|---|---|---|
| 5,663,559 A | 9/1997 | Auzerais et al. | |
| 5,947,213 A * | 9/1999 | Angle | E21B 47/002 175/24 |
| 6,378,627 B1 * | 4/2002 | Tubel | E21B 17/1078 175/24 |
| 7,139,219 B2 * | 11/2006 | Kolle | E21B 47/22 367/85 |
| 7,299,136 B2 * | 11/2007 | DiFoggio | G01V 1/50 702/22 |
| 7,634,059 B2 * | 12/2009 | Wraight | G01V 5/12 378/89 |
| 7,705,294 B2 | 4/2010 | Ramstad et al. | |
| 8,483,445 B2 | 7/2013 | Tjhang et al. | |
| 8,550,158 B1 * | 10/2013 | Shaposhnikov | E21B 43/26 166/247 |
| 9,228,401 B2 * | 1/2016 | Edwards | E21B 21/08 |
| 9,576,374 B2 * | 2/2017 | Elkington | G06T 7/13 |
| 10,174,578 B2 * | 1/2019 | Walton | C22C 21/00 |
| 10,509,141 B2 * | 12/2019 | Maeso | G01V 99/005 |
| 10,605,077 B2 * | 3/2020 | Aird | E21B 43/34 |
| 10,634,807 B2 * | 4/2020 | Tang | E21B 47/085 |
| 2008/0056604 A1 * | 3/2008 | Choe | G06T 5/003 382/269 |
| 2008/0192987 A1 * | 8/2008 | Helgason et al. | |
| 2009/0020333 A1 * | 1/2009 | Marsh | E21B 47/01 175/40 |
| 2009/0259446 A1 * | 10/2009 | Zhang | G06F 30/20 703/2 |
| 2014/0020954 A1 | 1/2014 | Pelletier et al. | |
| 2014/0046628 A1 | 2/2014 | Ligneul et al. | |
| 2014/0254884 A1 | 9/2014 | Elkington et al. | |
| 2014/0333754 A1 | 11/2014 | Graves et al. | |
| 2015/0330215 A1 | 11/2015 | Jamison et al. | |
| 2016/0370274 A1 | 12/2016 | Rowe et al. | |
| 2017/0058620 A1 | 3/2017 | Torrione | |
| 2017/0153355 A1 * | 6/2017 | Little, III | G01S 7/4818 |
| 2019/0368287 A1 | 12/2019 | Shekhar et al. | |
| 2019/0368347 A1 * | 12/2019 | Kulkarni | G01N 33/24 |
| 2020/0332654 A1 | 10/2020 | Rowe et al. | |
| 2022/0275694 A1 | 9/2022 | Shekhar et al. | |

FOREIGN PATENT DOCUMENTS

| | | |
|---|---|---|
| WO | 2009069004 A2 | 6/2009 |
| WO | 2013105930 A1 | 7/2013 |
| WO | 2015002653 A1 | 1/2015 |
| WO | 2015156893 A1 | 10/2015 |
| WO | 2016171650 A1 | 10/2016 |

OTHER PUBLICATIONS

PCT Application Serial No. PCT/US2019/032967, International Written Opinion, dated Aug. 23, 2019, 7 pages.
PCT Application Serial No. PCT/US2019/035002, International Search Report, dated Sep. 19, 2019, 3 pages.
PCT Application Serial No. PCT/US2019/035002, International Written Opinion, dated Sep. 19, 2019, 5 pages.
PCT Application Serial No. PCT/US2019/016548, International Search Report, dated May 20, 2019, 3 pages.
PCT Application Serial No. PCT/US2019/016548, International Written Opinion, dated May 20, 2019, 7 pages.
U.S. Appl. No. 16/959,014, Non-Final Office Action, dated Nov. 3, 2021, 13 pages.

* cited by examiner

IDENTIFYING A LINE OF COHERENT RADIATION IN A CAPTURED IMAGE OF ILLUMINATED DOWNHOLE PARTICLES

RELATED DISCLOSURE

This disclosure claims the benefit of priority under 35 U.S.C. § 119(e) of U.S. Provisional Application No. 62/680,675 filed Jun. 5, 2018 entitled "Edge Detection Using Coherent Radiation in Measurement of Drilled Cuttings", the contents of which are herein incorporated by reference in its entirety.

TECHNICAL FIELD

The disclosure generally relates to the field of hydrocarbon recovery operations, and more particularly to identifying a line of coherent radiation in a captured image of illuminated downhole particles, where the downhole particles are illuminated by the line of coherent radiation and/or ambient lighting. The identification of the line of coherent radiation facilitates determining features of the downhole particles such as size, volume, and shape of the particles

BACKGROUND

Borehole operations in a wellbore of a geologic formation produce particles. The particles include broken bits of solid material associated with drilling or fracturing operations such as rock. Return mud (also referred to as drilling fluid) from downhole carries the particles to the surface of a drilling platform. Via a flow line, the return mud travels to a shaker installed in a closed environment with low to dark ambient light or an open environment exposed to daylight or bright ambient light such as white light, tungsten light, infrared light, or light emitting diodes (LEDs). A top surface of the shaker is a screen which vibrates and causes fluids to fall through, leaving the particles on the screen. The screen is configured as a conveyor to move the particles from a first end to a second end of the shaker, resulting in the particles falling off the second end. The particles on the screen are analyzed in presence of the ambient light to determine features of the particles such as size, shape and volume of the particles. Based on the features of the particles, the borehole operations might be adjusted.

BRIEF DESCRIPTION OF THE DRAWINGS

Embodiments of the disclosure may be better understood by referencing the accompanying drawings.

DESCRIPTION

Figure 1:
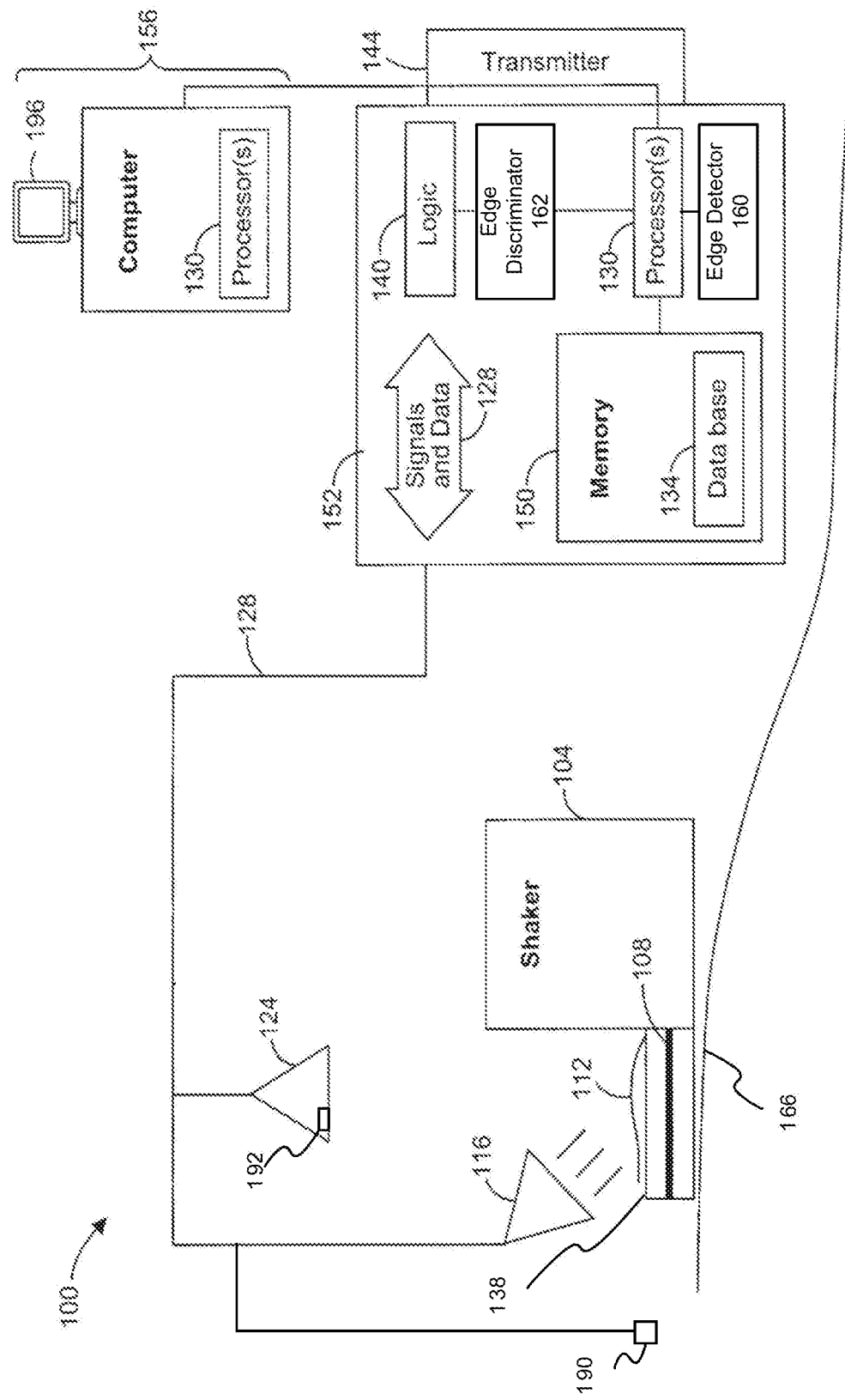
FIG. 1 is a block diagram of an example system for identifying a line of coherent radiation on a shaker screen of a shaker to facilitate analysis of the downhole particles.

The description that follows includes example systems, methods, techniques, and program flows that embody aspects of the disclosure. However, it is understood that this disclosure may be practiced without these specific details. For instance, this disclosure refers to identifying a line of coherent radiation in a captured image of illuminated downhole particles, where the downhole particles are illuminated by the line of coherent radiation and/or ambient lighting. Identification of the line of coherent radiation facilitate determining features of the downhole particles such as size, volume, and shape of the particles. Well-known instruction, protocols, structures and techniques have not been shown in detail in order not to obfuscate the description.

Overview

A line of coherent radiation directed along an end of the shaker screen of the shaker facilitates determining features of downhole particles. The line of coherent radiation is a laser line produced by a laser or some other coherent light device. As the particles pass under the line of coherent radiation, particles deflect the line of coherent radiation illuminating the particles as they pass over the end of the shaker screen. The particles are also illuminated by ambient light in the environment where the shaker screen is located.

An imaging device comprising one or more CCD (charge coupled device) cameras, including low light or infrared cameras captures an image of shaker screen. The captured image is processed by edge detection algorithms to identify image edges associated with the line of coherent radiation. The image edges indicate significant local intensity changes in the image typically due to the line of coherent radiation. These image edges are analyzed to determine the features of the particles which deflected the line of coherent radiation.

The ambient light adds excess light and noise in the vicinity of the line of coherent radiation, making detection of the line of coherent radiation difficult. Further, the location where the shakers are installed can be in zone 1/class 1/division 1 hazardous location installations requiring the laser which produces the line of coherent radiation to use low power to satisfy the specified limits for zone 1/class 1/division 1. The low power also makes identifying the line of coherent radiation difficult. The ambient lighting and/or reduced intensity of the laser results in the edge detection algorithm identifying image edges which are not associated with the line of coherent radiation, but rather due to intensity variation in the captured image due to noise from the ambient lighting and/or reduced intensity of the laser. These false detections of the line of coherent radiation result in errors in the determined features of the particles.

Various embodiments disclosed herein are directed to identifying the line of coherent radiation in presence of ambient lighting and/or reduced intensity of the laser. Images edges associated with the line of coherent radiation are distinguished from image edges associated with intensity variation in the captured image due to the ambient lighting and/or reduced intensity of the laser. By identifying these image edges, the line of coherent radiation is positively identified and features of the particles including one or more of size, shape, and volume of the particles are more accurately determined.

In one or more examples, an edge detection algorithm applied to the captured image produces a gradient plot which indicates edge strength of image edges detected in the captured image as a function of position in the captured image. A pattern of the image edges in the gradient plot indicates that the image edges are associated with the line of coherent radiation. This pattern includes a rising edge followed by a falling edge. This pattern includes the rising edge and falling edge having an amplitude within a certain percentage of each other. The percentage is based on an intensity of the line of coherent radiation. Based on detection of this pattern, the line of coherent radiation is identified and analyzed to determine features of the particles.

In one or more examples, image edges in the gradient plot associated with the line of coherent radiation has a pattern where a distance between the rising edge and falling edge is a defined distance. The defined distance is proportional to a width of the line of coherent radiation such as 2-5 millimeters. If the distance between peaks matches the defined distance, then the image edges are associated the line of coherent radiation. The line of coherent radiation is identified and analyzed to determine features of the particles. If the distance between peaks does not match the defined distance, then the image edges are not associated with the line of coherent radiation. The line of coherent radiation is not identified.

In one or more examples, amplitude of the rising edge and falling edge indicates whether the image edges in the gradient plot are associated with the line of coherent radiation. If the amplitude of the rising and falling edge are greater than a minimum edge strength, then the image edges are associated with the line of coherent radiation. The line of coherent radiation is identified and analyzed to determine features of the particles. If the amplitude of the rising and falling edge are less than the minimum edge strength, then the image edges are not associated with the line of coherent radiation. The line of coherent radiation is not identified. Some shaker installations are exposed to the bright/ambient light. A photoelectric sensor which can sense the ambient light feeds a value indicative of the ambient light to processing system and the minimum edge strength is adjusted based on the value indicative of the ambient light. Photoelectric sensor can be a simple LDR (Light Dependent Resistor), Lux meter or a component/device/instrument which can feed the ambient light readings to the processing system.

In one or more examples, color of pixels in the captured image facilitates identification of the line of coherent radiation. The line of coherent radiation has a defined color, for example, characterized by red, green, blue component (RGB) values, based on the laser which produces the line of coherent radiation. Pixels of the captured image have also component values characterized by, for example, RGB values. In presence of variable ambient lighting, the color of the pixels associated with the line of coherent radiation in the captured image will be different from the defined color. If the difference is more than a threshold amount, then the ambient light will prevent accurate identification of the line of coherent radiation. Detection is stopped and/or the condition is reported as a fault.

Use of one or more of the described examples to detect whether image edges in a gradient plot are associated with a line of coherent radiation increases the accuracy in identifying the line of coherent radiation and determining features of the particles such as one or more of size, shape, and volume. With this more accurate determination, recovery of hydrocarbons from downhole can be adjusted to maximize production.

It is understood that this disclosure may be practiced without certain specific details. In other instances, well-known structures and techniques have not been shown in detail in order not to obfuscate the description.

Example System

FIG. 1 is a block diagram of an example system 100 for identifying a line of coherent radiation on a shaker screen 108 of a shaker 104 to facilitate analysis of downhole particles. The system 100 comprises a combination of an imaging device 124, laser 190-192, and one or more processors 130 for illuminating a downhole particle 112 on the shaker screen 108 of the shaker 104 with a line of coherent radiation and identifying the line of coherent in presence of ambient light. The identification of the line of coherent radiation also facilitates determining features of the downhole particle such as size, volume, and shape of the particle. The term particle as used herein may refer to one particle or a plurality of particles. The imaging device 124 and/or the processors 130 may be located at a surface 166 of a geological formation, and form part of a data acquisition system 152. In some examples, any of the components in FIG. 1 may be located below the surface 166.

The system 100 may also include logic 140. The logic 140 can be used to acquire live video stream information 128 from the imaging device 124 such as image data, and data from downhole, including depth of the drill bit during a drilling operation or depth of a fracturing operation.

A memory 150, located above or below the surface 166, can be used to store acquired image data, as well as the data downhole (e.g., in a database 134). The memory 150 is communicatively coupled to the processor(s) 130.

The imaging device 124 may comprise one or more CCD (charge coupled device) cameras, including low light or infrared cameras, to capture images of downhole particles such as downhole particles 112 (also referred to herein as particles) deposited on the shaker 104, such as on the shaker screen 108 (also referred to herein as a "shaker screen" or generally "screen") resulting from borehole operations. The shaker screen 108 may form part of the shaker deck 138, such as a shale shaker deck. Thus, the shaker screen 108 may be included in the shaker deck 138. The cameras may be focused on the shaker screen 108 to capture images of particles 112 as they move across one or more shakers 104.

Elements can be added to the path of energy travel to selectively reduce an amount of energy received by the imaging device 124. Thus, the system 100 may comprise polarizers, filters, or beam splitters to intercept energy reflected or emitted by the particles 112, and to reduce the amount of the energy received by the imaging device 124.

Imaging device 124 may comprise, for example, a pco 4000 CCD camera from Adept Turnkey Pty Ltd. with 4008×2672 pixel resolution for the visible light spectrum. If the conditions are such that a high sensitivity line scan camera may be useful, a Piranha HS-80-08K40 camera or Piranaha HS-40-04K40 camera, also from Adept Turnkey Pty Ltd. can be used. For near infrared imaging, an XEVA-FPA-1.7-640 camera from the LOT-Oriel Group Europe with an InGaAs array at 640×512 resolution can be used. For mid infrared imaging, a VarioTHERM® InSb camera from JENOPTIK Optical Systems Inc. with an InSb array at 640×512 resolution can be used. For far infrared detection, a Photon 640 camera from FLIR Systems, Inc. can be employed. Other imaging devices can also be used.

The system 100 also includes one or more lasers or other coherent light device. In this example, a laser 192 that is incorporated into the imaging device 124 is positioned above the particles 112. In addition or instead of laser 192, the system 100 might include a laser 190 positioned to a side of the particles 112. The system 100 can include more or less lasers. For example, the system 100 can include additional lasers at other positions relative to the particles 112. The lasers 190-192 can emit a line of coherent radiation onto the particles 112, which illuminate the particles 112 as they pass under the line of coherent radiation and deflect the line of coherent radiation.

The system 100 may be located in low or dark ambient conditions to facilitate image capture of the downhole particles on the shaker screen 108. In some examples, the system 100 may include an illumination source 116 to facilitate the image capture. The illumination source 116 may comprise white lights for CCD cameras or near, mid, or far wave infrared lights. In other examples, the illumination source 116 might be daylight or associated with ambient light. The ambient light and/or illumination source also illuminates the particles 112.

The imaging device 124 can be connected to the data acquisition system 152, perhaps including the logic 140, and then to a computer (comprising one or more processors 130) associated with a remote workstation 156, or directly to the computer. While a depiction of a computer and workstation is shown, some examples can be any type of device or apparatus to perform operations described herein. The video stream information 128, or a processed form of the information, can be sent to the remote workstation 156 via coaxial cable or Ethernet cable. For longer data transmission distances, and to reduce the magnitude of possible interference, the video stream information 128 may be converted to an optical format and sent to the remote workstation 156 via fiber optic transmission. A transmitter 144 may be used to send the video stream information 128 or a processed form of the information, to the remote workstation 156 via wires, fiber optics, or wirelessly.

The computer may determine features of the particles 112 such as size, volume, and shape by analyzing captured images associated with the video stream information 128. The analysis may be performed in real time or off-line. For example, the processor(s) 130 may be configured to process the video stream information 128 to determine data that quantifies the size, volume, and shape of the particles. The processor(s) 130 may also be configured to publish changes in the size, volume, and shape of the particles in conjunction with probable conditions associated with a borehole drilling operation or a borehole fracturing operation. Alternatively, or in addition, the processors 130 can modify the borehole operations based on size, volume, and shape of the particles.

Programs that provide face recognition and particle size analysis are commercially available to determine the features of the particle. Three-dimensional face recognition software can be used to identify more than just the general shape of particles—the volume distribution of the particles can also be determined. The software can be trained or modified to identify particle shapes, to determine volume distribution, and to provide data in a form that various monitoring software, such as Halliburton's INSITE Anywhere® web delivery system, can process.

These recognition and analysis programs include software that is similar to or identical to PAX-it image management and analysis software by MIS Inc. of Villa Park, Ill. and the Split-Online® automated digital image analysis system from Split Engineering LLC, as well as the SureMatch 3D facial recognition software suite available from Genex Technologies, Inc. of Bethesda, Md. Other software and processing instructions may be used, based on technical needs and flexibility.

The recognition and analysis programs typically operate under the principle that the particles 112 pass under the line of the coherent radiation and deflect the line of coherent radiation as a result of contacting the particles 112. The deflection may be indicative of features of the particles 112 such as size, volume or shape. An amount of the deflection may indicate the size and surface area of the particles 112. Volume of the particles 112 can be obtained by multiplying the surface area of the particles 112 (determined by laser 190 and/or 192 deflection) to a velocity of particles 112 passing under the line of coherent radiation. The velocity of the particles 112 may be determined using an approach of tracking a particle over a certain distance for a certain amount of time. The imaging device 124, in conjunction with a velocity capture algorithm can be used to track the velocity of the particles 112. Other methods using radars may also be used to determine velocity of the particles 112.

The system 100 includes an edge detector 160 to facilitate identification of the line of coherent radiation for purposes of determining the features of the particles 112. The edge detector 160 detects significant intensity changes in the captured image such as dark to bright zones or vice versa. The significant intensity changes are referred to as image edges. The image edges are detected by applying various edge detection algorithms including Roberts edge detection, Sobal edge detection, Canny edge detection, Prewitt edge detection, Kirsch edge detection, Robinson edge detection, Marr-Hildreth edge detection, and LoG edge detection to pixels of the captured image. The edge detection algorithms identify the image edges in a gradient plot of edge strength as a function of position on the shaker deck 138. The image edges are typically associated with the line of coherent radiation. Based on identification of the line of coherent radiation, the recognition and analysis programs can determine deflection of the line of coherent radiation and features of the particles 112 such as size, volume, and shape.

Some shakers 104 are installed in a closed environment with low to dark ambient light. The low to dark ambient light allows for accurately identifying the line of coherent radiation. Other shakers 104 are installed in area which are exposed to daylight or bright ambient light such as white light, tungsten light, infrared light, or light emitting diodes (LEDs). The daylight or bright ambient light adds primary colors to the vicinity of the line of coherent radiation, making identification of the line of coherent radiation difficult. Further, the location where the shakers 104 are installed can be in zone 1/class 1/division 1 hazardous location installations. In this regard, the laser 190, 192 which produces the line of coherent radiation is also required to use low power to satisfy the specified limits for zone 1/class 1/division 1. The low power also makes identifying the line of coherent radiation difficult. The edge detector 160 may identify illumination of the particles 112 by the ambient lighting as image edges but which are not associated with the line of coherent radiation and illumination of the particles 112 by the laser having low power as not being associated with the line of coherent radiation. These false detections result in errors in identification of the line of coherent radiation.

To reduce the errors, the logic 140 may also have an edge discriminator 162 that processes an output of the edge detector 160 (e.g., gradient plot) to discriminate between image edges associated with the line of coherent radiation and image edges associated with intensity variation in the captured image due to noise from the ambient lighting and/or reduced intensity of the laser 190, 192. The edge discriminator 162 may discriminate between image edges in many ways. Based on this discrimination, the line of coherent radiation can be identified.

In one example, image edges associated with the line of coherent radiation in the gradient plot may have a given pattern of peaks. The image edges which have the given pattern of peaks is associated with the line of coherent radiation. As another example, the image edges associated with the line of coherent radiation in the gradient plot may be discriminated by a center distance or time between a positive and negative peak. The image edges associated with the line of coherent radiation may have peaks separated by a given distance indicative of a line of coherent radiation. As yet other example, color of the pixels associated with the peaks may be compared to color of the line of coherent radiation. In presence of variable ambient lighting, the color of the pixels associated with the line of coherent radiation in the captured image will be different from the defined color. If the difference is less than a threshold amount, then line of coherent radiation can be identified. If the difference is more than a threshold amount, then the line of coherent radiation cannot be identified. Edge detection is stopped and/or the condition is reported as a fault. As another example, an amplitude of a peak exceeding a threshold amount indicates that the image edge associated with the peak is associated with the line of coherent radiation.

By identifying image edges associated with the line of coherent radiation in the gradient plot as disclosed, the line of coherent radiation can be identified and features of the particles can be more accurately determined.

Example Drilling Application

Figure 2:
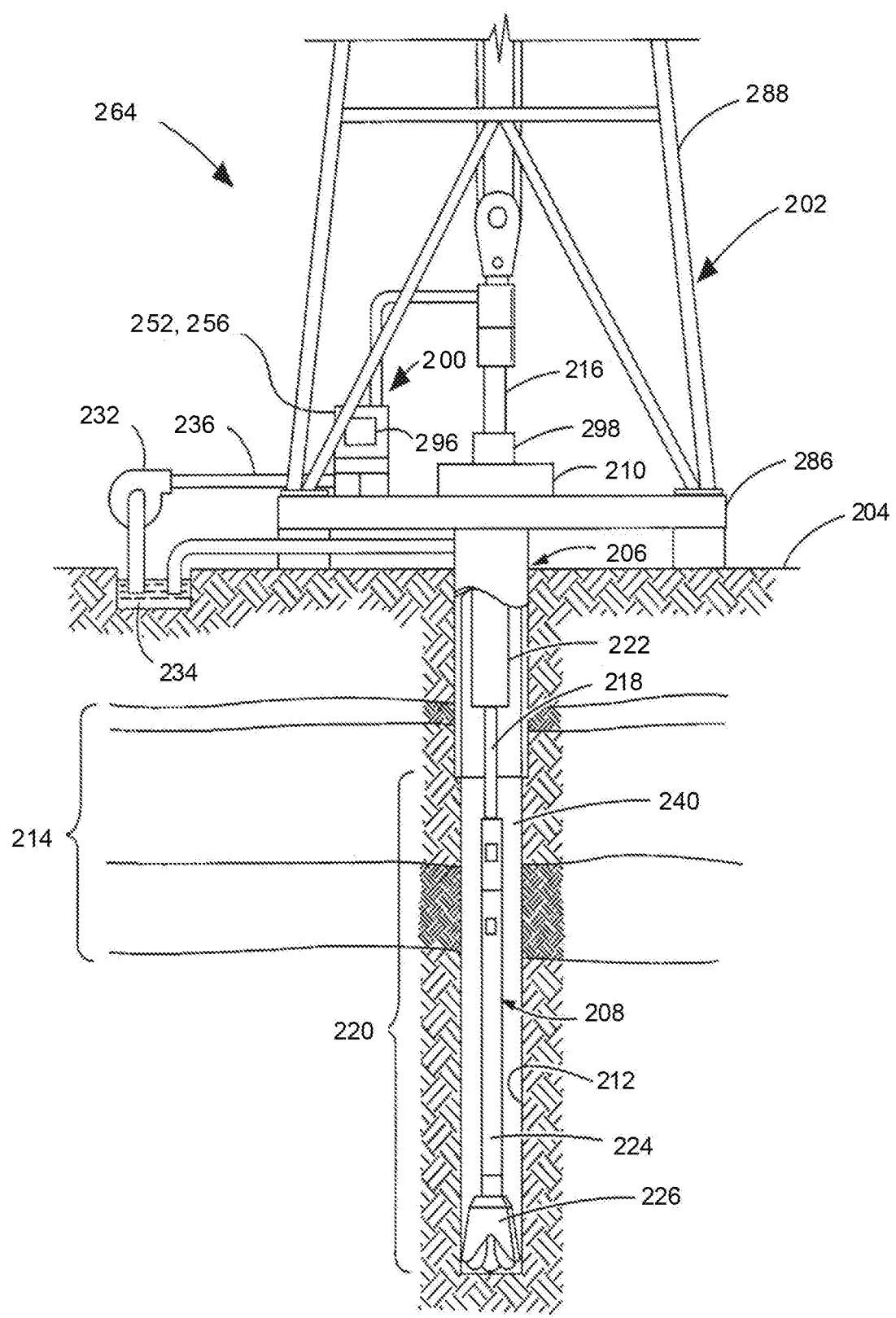
FIG. 2 is a schematic diagram of an example drilling rig system.

FIG. 2 is a schematic diagram of a drilling rig system 264, according to some embodiments in which the line of coherent radiation is detected and features of the particles are determined. The system 264 may form a portion of a drilling rig 202 located at the surface 204 of a well 206. Drilling of oil and gas wells is commonly carried out using a string of drill pipes connected together so as to form a drilling string 208 that is lowered through a rotary table 210 into a wellbore or borehole 212. Here a drilling platform 286 is equipped with a derrick 288 that supports a hoist.

The drilling rig 202 may thus provide support for the drill string 208. The drill string 208 may operate to penetrate the rotary table 210 for drilling the borehole 212 through subsurface formations 214. The drill string 208 may include a kelly 216, drill pipe 218, and a bottom hole assembly 220, perhaps located at the lower portion of the drill pipe 218.

The bottom hole assembly 220 may include drill collars 222, a down hole tool 224, and a drill bit 226. The drill bit 226 may operate to create a borehole 212 by penetrating the surface 204 and subsurface formations 214. The down hole tool 224 may comprise any of a number of different types of tools including MWD tools, LWD tools, and others.

During drilling operations, the drill string 208 (perhaps including the kelly 216, the drill pipe 218, and the bottom hole assembly 220) may be rotated by the rotary table 210. In addition to, or alternatively, the bottom hole assembly 220 may also be rotated by a motor (e.g., a mud motor) that is located down hole. The drill collars 222 may be used to add weight to the drill bit 226. The drill collars 222 may also operate to stiffen the bottom hole assembly 220, allowing the bottom hole assembly 220 to transfer the added weight to the drill bit 226, and in turn, to assist the drill bit 226 in penetrating the surface 204 and subsurface formations 214.

During drilling operations, a mud pump 232 may pump drilling fluid (sometimes known by those of ordinary skill in the art as "drilling mud") from a mud pit 234 through a hose 236 into the drill pipe 218 and down to the drill bit 226. The drilling fluid can flow out from the drill bit 226 and be returned to the surface 204 as through an annular area 240 between the drill pipe 218 and the sides of the borehole 212. The drilling fluid returning back to the surface is sometimes referred to as "return mud." The drilling fluid may be returned to the mud pit 234, where such fluid is filtered. In some embodiments, the drilling fluid can be used to cool the drill bit 226, as well as to provide lubrication for the drill bit 226 during drilling operations. Additionally, the drilling fluid may be used to remove subsurface formation 214 particles created by operating the drill bit 226. It is the images of these particles that embodiments operate to acquire and process.

Thus, referring now to FIGS. 1-2, it may be seen that in some embodiments, a system 264 may comprise a shaker screen 108 to receive the drilling mud, and one or more image processing system 100 as described previously. The system 100 may be configured to have a field of view that includes the shaker screen 108, wherein the system 100 includes one or more imaging devices 124 and one or more processors 130, operating as described previously.

The shape, size, and/or volume of particles can be displayed to show changes that have occurred, and the operational conditions that are likely to be associated with those types of changes. Thus, the system 264 may comprise a display 196 to display the changes and the probable conditions. These conditions may be used to implement real-time drilling control in some embodiments (e.g., if falling shale is indicated by a dramatic increase in volume, the weight on the bit may be reduced, or drilling may be halted entirely).

A transmitter can be used to send the data (e.g., volume) to a remote location, such as a workstation 156, perhaps for alarming, further processing/analysis, or real-time operational control. Thus, a system 264 may comprise a transmitter 144 to transmit at least a portion of the data to a remote processor. Many embodiments may thus be realized.

It should also be understood that the apparatus and systems of various embodiments can be used in applications other than for pumping and drilling operations, and thus, various embodiments are not to be so limited. The illustrations of system 100 and systems 264 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules. Such apparatus and systems may further be included as sub-components within a variety of electronic systems, such as televisions, cellular telephones, personal computers, workstations, radios, video players, vehicles, signal processing for geothermal tools and smart transducer interface node telemetry systems, among others. Some embodiments include a number of methods.

A rig is typically surveyed to determine number of shakers present and number of needed cameras to cover shaker surface area. Determination can be made whether cameras will need support structure or can be mounted on surface with line of sight of the shaker. Determination whether additional lighting is needed can also be made. Cameras with lasers can be sent to rig site with computers setup to handle the data rate for processing and analyzing the particles. Lasers can be used to determine depth of investigation and as a point of reference. Cameras can be mounted on a support structure or other flat surface that gives line of sight of the shakers A communication cable and possible power cable can be run from nearest point of power and data acquisition point. The data acquisition point can be a computer of some other device with the capability to interpret or transmit the pictures to a software program. The software program may or may not have to be calibrated using objects with a known volume that may or may not be of different shapes. The calibration could occur on the shakers themselves or on another flat surface with the same focal length To determine the depth that the particles from which the particles originate downhole, bit depth and lag can be monitored. Bit depth can be derived from the amount of pipe in the borehole. For example, bit depth can be based on the number of joints of pipe in the hole and knowing the length of all the joints or by monitoring the draw works and determining how much the block has traveled while adding pipe to the borehole. Lag can be determined based on a location of the drill bit, the pump rate in either strokes or volume per unit of time, and the volume of the annulus.

When a foot of formation is drilled and knowing the bit and reamer size, the volume of formation can be calculated based on a unit of depth of the formation that has been drilled, the size of the drill bit, and size of the reamer. The return of this volume of formation to the surface can be determined based on the lag.

The workstation 156 may maintain a discrete or cumulative volume of particles per discrete depth interval or/and as a discrete cumulative volume of particles per discrete time. The data in the form of pictures and/or volumes may be stored at the well site and/or transmitted off site. If drilling fluid is not removed from the particles 112, an erroneous volume would be calculated. If shaker screens 108 become flooded with particles or fluid, an erroneous volume would also be calculated. In one or more embodiments, the drilling fluid maintained on the particles 112 will not calculated and no method will be used to remove wetting of particles. The drilling fluid left on particles can be considered an error of measurement.

Figure 3:
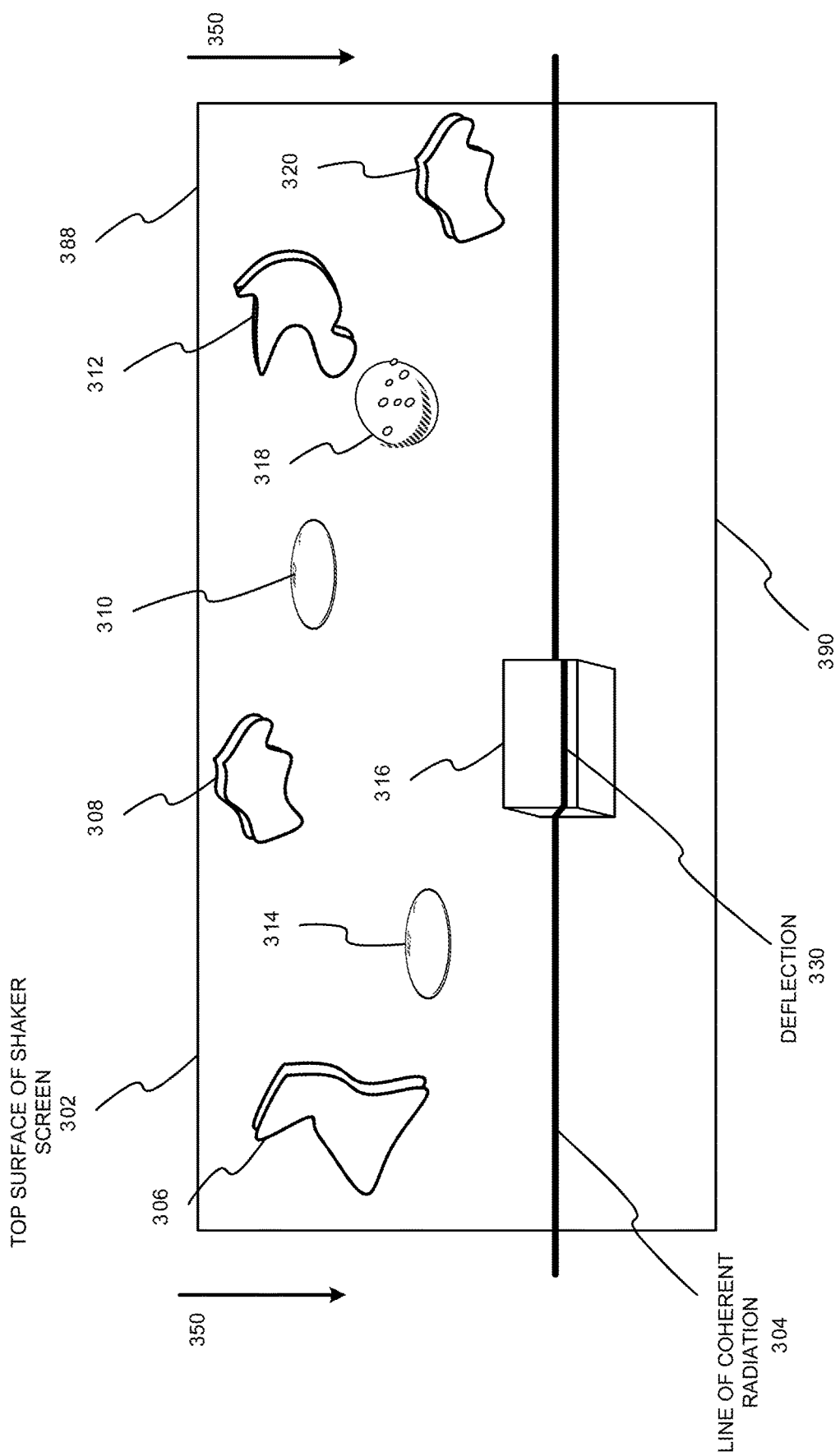
FIG. 3 is a schematic diagram of an example top surface of a shaker with a number of downhole particles and a line of coherent radiation.

FIG. 3 is a schematic diagram of the field of view associated with the system 100. The field of view 300 includes viewing a number of particles 306-320 on a top surface 303 of the shaker screen and a line of coherent radiation 304 on the top surface 302 of the shaker screen. As shown, the particles 306-320 can be any shape and size. Initially, the particles 306-320 are placed at or near an end 388 of the shaker screen and move in a direction shown by arrows 350 to an end 390 of the shaker screen to separate the particles from the drilling fluid. The particles 306-320 then fall off the end 390. The line of coherent radiation 304 is emitted from the laser 190, 192 onto the top surface 302 at or near the end 390. In this example, the particle 316 causes a deflection 330 of the line of coherent radiation 304 as it passes under the line of coherent radiation 304. The imaging device captures all or a portion of the field of view 300 including illumination of the particle 316 by the deflection 330 and illumination by ambient light as an image which is processed to identify the line of coherent radiation and determine features of the particle including a size, volume and shape of the particle 316. The particles 306-322 may be analyzed in other ways as well.

Example Gradient Plots

The line of coherent radiation on the top surface of the shaker screen produces significant local change in intensity in the image captured by the imaging devices such as dark to bright zones or vice versa in the captured image. The line of coherent radiation in the captured image is identified by the significant local changes. The significant local changes are shown as image edges in the gradient plot output by the edge detection algorithms which need to be distinguished from other edges resulting from illumination of downhole particles by ambient light and the line of coherent radiation. Based on the identification of the line of coherent radiation, features of the particles can be determined such as size, volume, and shape due to deflection of the line of coherent radiation.

Figure 4:
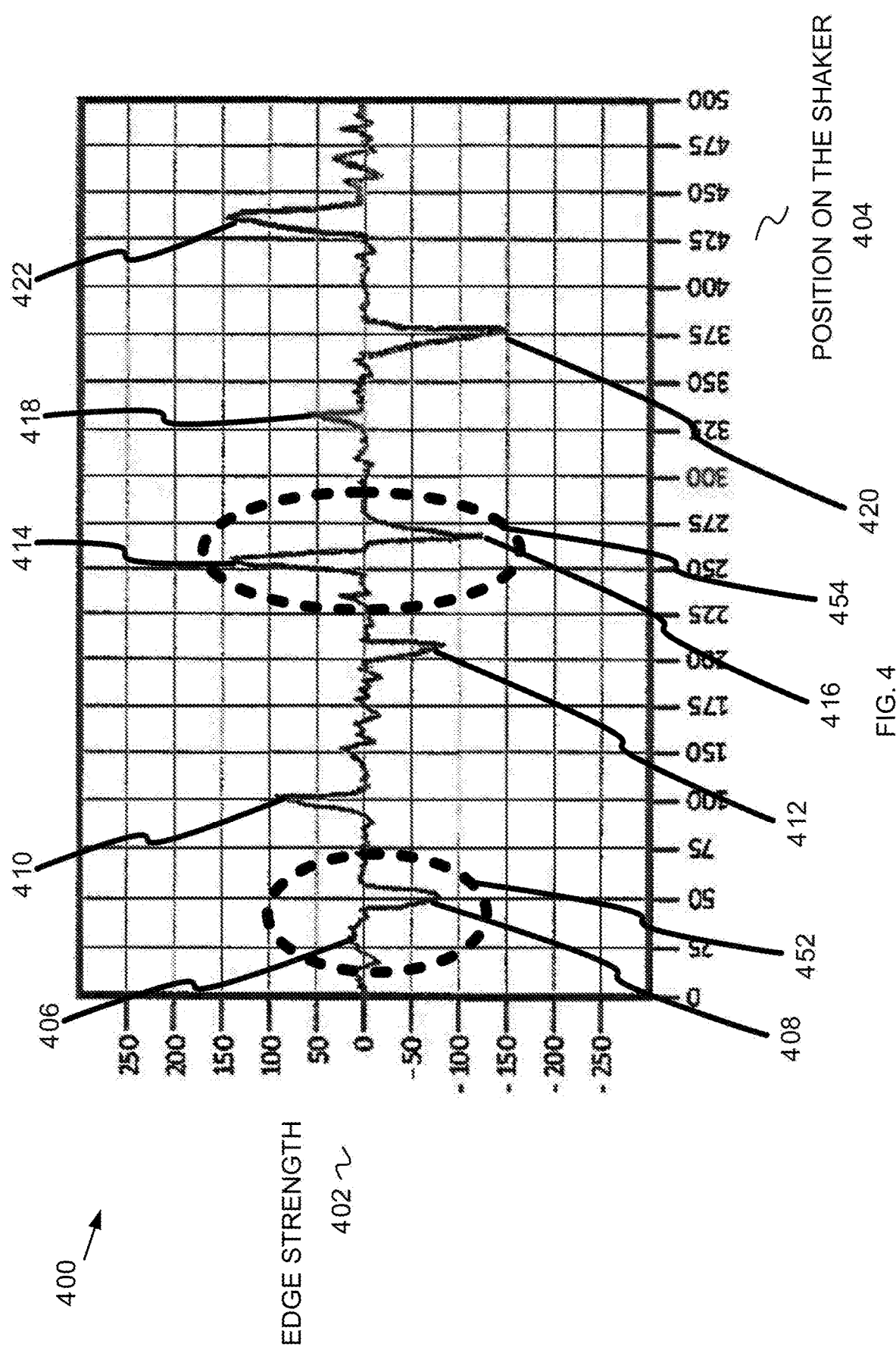
FIG. 4 depicts a first example gradient plot of edge strength associated with a captured image of the top surface of the shaker.

FIG. 4 depicts a first example gradient plot 400 associated with a captured image. The gradient plot 400 includes a y-axis 402 which indicates edge strength associated with image edges in the captured image and an x-axis 404 associated with a position along the shaker screen. The position may be along a direction of arrow 350 in FIG. 3 which crosses over the line of coherent radiation, or in some other linear or non-linear direction. The gradient plot 400 includes multiple image edges such as rising and falling edges. In this example, the gradient plot 400 includes a rising edge 406, a rising edge 410, a rising edge 414, a rising edge 418, and a rising edge 422. The gradient plot 400 also includes a falling edge 408, a falling edge 412, a falling edge 416, and a falling edge 420.

The line of coherent radiation has high intensity in the captured image. In this regard, a pattern of rising and falling edges is associated with the line of coherent radiation. The pattern includes a rising edge indicative of a transition from low intensity to high intensity in the captured image immediately followed by a falling edge indicative of transition from the high intensity to low intensity in the captured image. The pattern also includes an edge strength value of the rising edge and falling edge within a certain percentage of each other. Groupings 452 and 454 illustrate examples of the image edge not meeting and meeting the pattern, respectively.

The grouping 452 includes a rising edge 406 followed after a period of time by a falling edge 408. The rising edge 406 is not immediately followed by a falling edge 408. The certain percentage of the edge strength value of the rising edge and falling edge may be 25% which might not be within the certain percentage. The grouping 452 is considered noise and not an image edge associated with the line of coherent radiation.

A grouping 454 includes a rising edge 414 immediately followed by a falling edge 416. The rising edge 414 immediately follows the falling edge 416 if a distance between the rising edge 414 and falling edge 416 is correlated to a width of the line of coherent radiation. (e.g., between 2-5 millimeters). The width of the line of coherent radiation may be measured during a calibration when no particles are on the shaker screen or known based on design of the laser which outputs the line of coherent radiation. Further, an edge strength value of the rising edge 406 and an edge strength value of the falling edge 408 may be 80% which might be within the certain percentage. The grouping 454 is considered an image edge associated with a line of coherent radiation.

Figure 5:
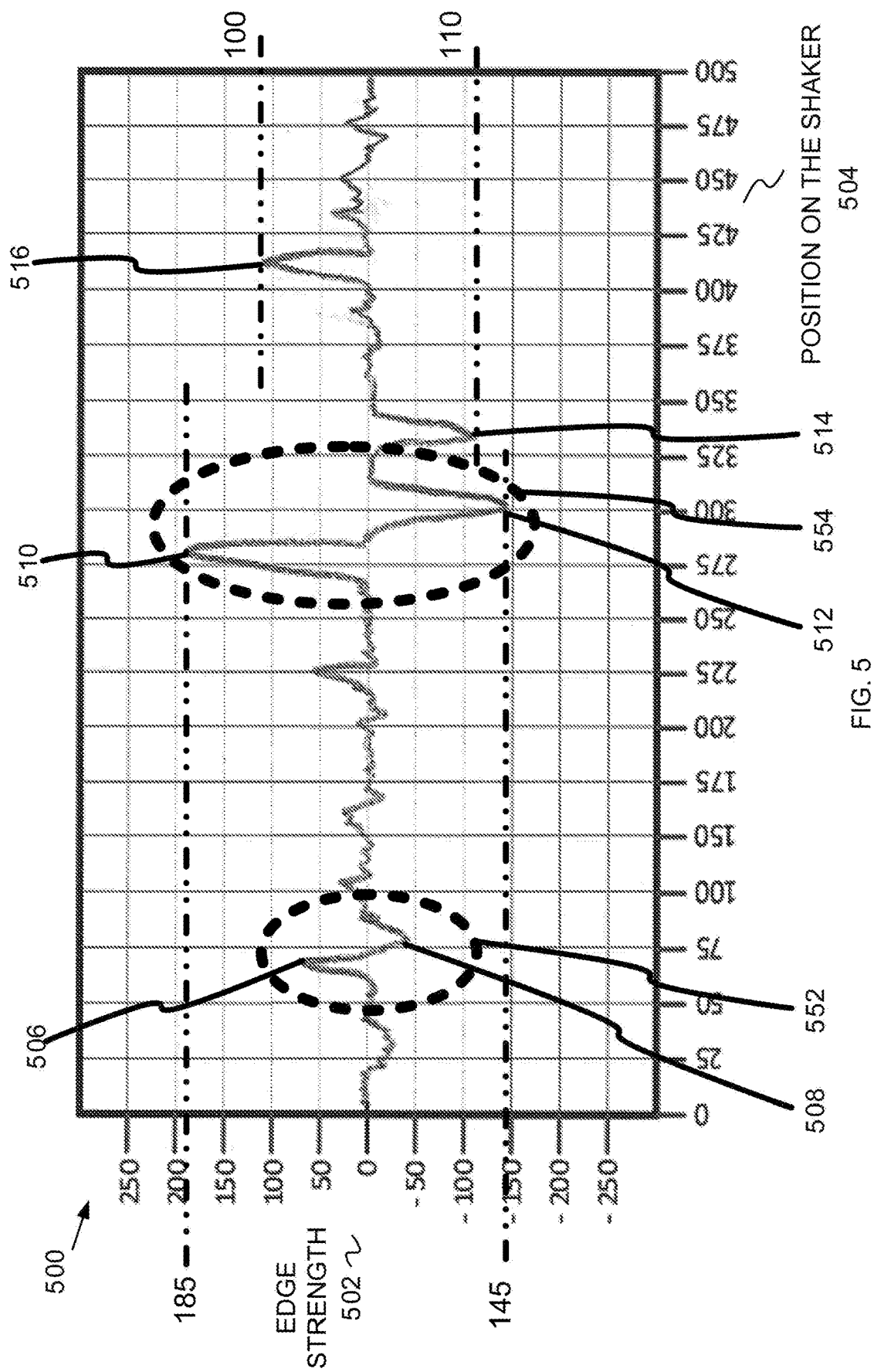
FIG. 5 depicts a second example gradient plot of edge strength associated with a captured image of the top surface of the shaker.

FIG. 5 depicts another example gradient plot of edge strength versus position associated with a captured image. Gradient plot 500 includes a y-axis 502 of edge strength and an x-axis 504 of a position along the shaker screen. The gradient plot 500 also includes multiple rising edges and falling edges. In this example, the gradient plot 500 includes a rising edge 506, a rising edge 510, and a rising edge 516. The gradient plot 500 also includes a falling edge 508, a falling edge 512, and a falling edge 514. An edge strength value of the rising edge 510 is 185. An edge strength value of the rising edge 516 is 100. An edge strength value of the falling edge 512 is 145. An edge strength value of the falling edge 514 is 110. The rising and/or falling edge may have a minimum edge strength value to be associated with the line of coherent radiation. In this regard, group 552 may be considered noise because the rising and/or falling edges do not meet a minimum edge strength value while group 554 might include image edges associated with a line of coherent radiation because the rising and/or falling edges meet the minimum edge strength.

The minimum edge strength value may be determined during a calibration process. For example, a calibrated edge strength of the line of coherent radiation may be determined by identifying an image edge associated with the line of coherent radiation. The image edge may be in a gradient plot of an image of the shaker screen when no particles are on the shaker screen. The image edge may have an edge strength value and the minimum edge strength value may be based on the edge strength value. The minimum edge strength value may be determined under no ambient light and/or ambient light. The minimum edge strength value facilitates identifying image edges associated with the line of coherent radiation from image edges associated with the ambient light.

The minimum edge strength value may be adjusted for various reasons. For example, the minimum edge strength value may be adjusted based on ambient light. Greater and/or variable amounts of ambient light may cause the minimum edge strength value to be lower while lesser and/or constant amounts of ambient light may cause the minimum edge strength value to be higher. To facilitate this adjustment, a photoelectric sensor may sense the ambient light and feed the real time ambient light to a processing system which dynamically adjusts the minimum edge strength. The photoelectric sensor can be a simple LDR (Light Dependent Resistor), Lux meter or any component/device/instrument which can feed the ambient light readings adjust the minimum edge strength. Further, some kind of shrouding might be also placed over the shaker to avoid the direct exposure of the shaker screen to sunlight.

Another reason to adjust the minimum edge strength value may be if the laser is out of operation, causing no line of coherent radiation to be emitted onto the top surface of the shaker screen. In this situation, detection of image edges associated with particle edges is not possible and the minimum edge strength might be some maximum edge strength value to disable any detection.

Yet another reason to adjust the minimum edge strength value may be if the line of coherent radiation is blocked (partially or fully) from being displayed on the top surface of the shaker screen. For example, transparent obstacles (e.g., fumes, gases, water vapors, etc.) may be in between the laser source and end of the shaker screen and reduce the intensity of the detected laser line. More blockage causes the minimum edge strength value to be lower. Less blockage causes the minimum edge strength value to be higher.

Another reason to adjust the minimum edge strength value may be if the laser has a hardware fault (e.g., end of operational life of the coherent radiation emitter, low power supply, etc.), which reduces intensity of the line of coherent radiation being emitted. Less intensity results in reducing the minimum edge strength. The minimum edge strength may be adjusted for other reasons as well.

If there is intrusion of ambient light in the vicinity of the line of coherent radiation, image edges may be falsely identified as being associated with the line of coherent radiation. To reduce chances of such a false detection, a color of one or more pixels associated with the captured image and a color of the line of coherent radiation when output by the laser are compared. The color of the line of coherent radiation output by the laser may be known based on design of the laser used to generate the line of coherent radiation. Different type of lasers may output different colors of coherent radiation. Alternatively, the color may be measured near an output of the laser so that the measurement is not affected by ambient lighting. Both the color of the line of coherent radiation output and the color of the pixels associated with image edges may be identified by red, green, and blue (RGB) component values. An intensity of one or more of RGB values associated with the line of coherent radiation output can be compared to respective intensity of RGB values of the pixels associated with the image edge. In one or more examples, the G components will be compared. In case of variable lighting (higher than ambient), one or more of the RGB values associated with the image edges will differ from the RGB values of the line of coherent radiation output. Excess light is a deterrent to edge detection. If the difference resulting from the comparison exceeds a threshold, then an alarm can be generated to notify an operator of this condition.

Example Operations

Figure 6:
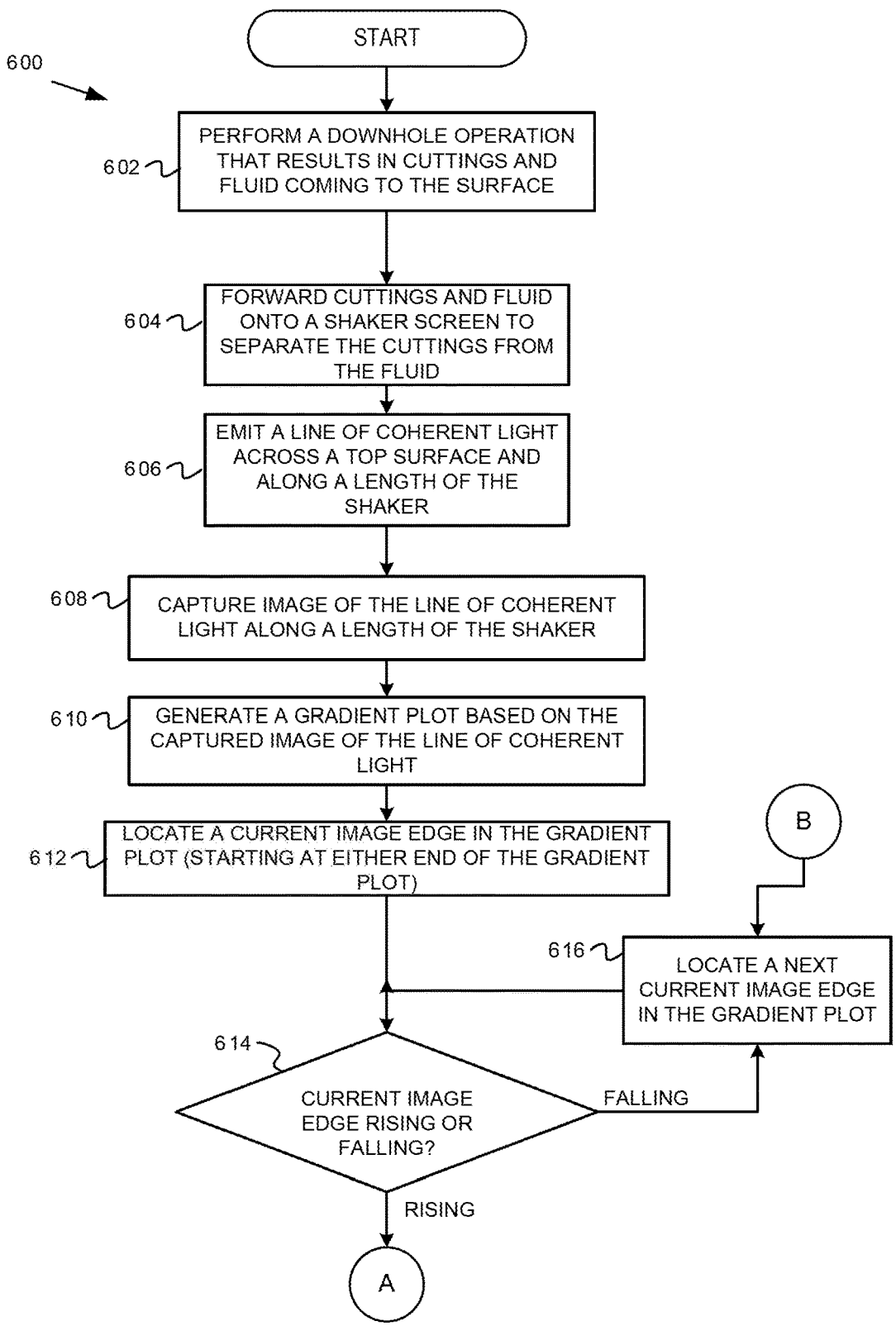
FIGS. 6-7 are example flowcharts of operations for identifying the line of coherent radiation in the captured image and determining size, volume, and shape of the downhole particles.
Figure 7:
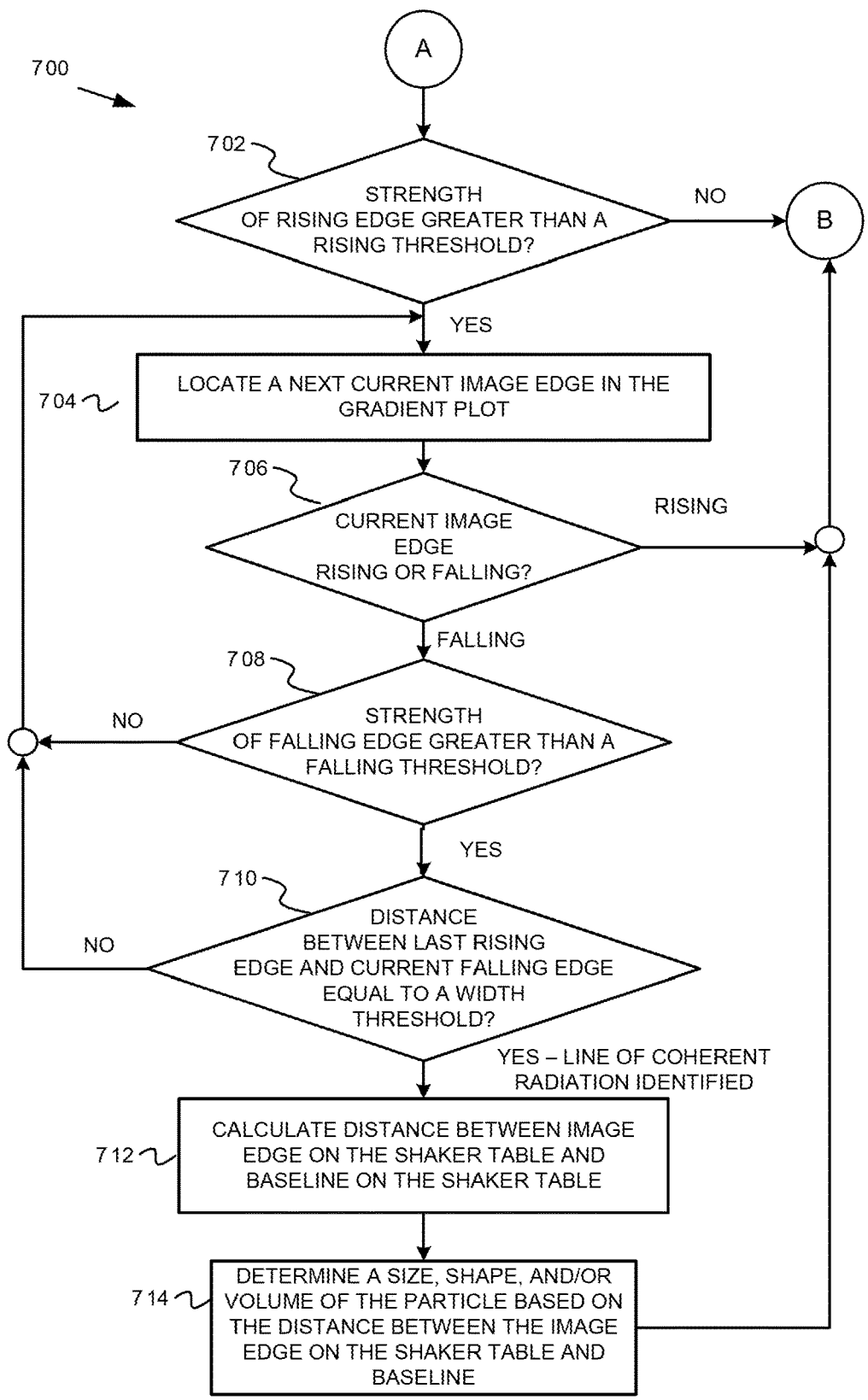

Example operations for identifying the line of coherent radiation in the captured image and determining size, volume, and shape of the particles are now described. FIGS. 6-7 are flowcharts 600-700 which continue between each other through transition points A-B. Operations of the flowcharts 600-700 can be performed by software, firmware, hardware or a combination thereof. The operations of the flowchart 600 start at block 602.

At block 602, a downhole operation is performed that results in particles and fluid coming to the Earth's surface. The downhole operation may be drilling, but also could be fracturing, etc.

At block 604, the particles and fluid are forwarded onto a shaker screen to separate the particles from the fluid.

At block 606, a line of coherent light is emitted across a length of the shaker screen. For example, the line of coherent light can be emitted across the length of the shaker at or near the end where the particles are to fall after being separated from the fluid based on the vibration of the shaker (as the fluid falls through the openings of the shaker screen).

At block 608, an image of the line of coherent light along the length of the shaker is captured. This image can include any deflections of the line of coherent light caused by the particles moving under the line of coherent light.

At block 610, a gradient plot is generated based on the captured image of the line of coherent radiation. The gradient plot indicates one or more areas of significant pixel intensity variation in the captured image, identified as image edges. The horizontal axis of the gradient plot may correspond to a spatial position over the shaker while the vertical axis may indicate an edge strength.

At block 612, an image edge in the gradient plot is located (starting at either end of the gradient plot). The image edge may be a rising or falling edge. For example, the gradient plot can be processed starting on the left side of the gradient plot.

At block 614, a determination is made whether the current image edge is rising or falling. If falling, operations of the flowchart 600 continue at block 616. If rising, operations of the flowchart 600 continue at transition point A, which continues at transition point A of the flowchart 700.

At block 616, a next image edge in the gradient plot is located. For example, the next image edge in the gradient plot can be located continuing from left to right (after the previously located image edge). Operations of the flowchart return to block 614, where a determination is made of whether the next image edge located is rising or falling.

Operations continue in the flowchart 700. From transition point A, operations continue at block 702 (after it was previously determined that the current rising or falling edge is rising).

At block 702, a determination is made of whether an edge strength of the rising edge exceeds a minimum edge threshold. If the edge strength of the rising edge does not exceed the minimum edge threshold, operations continue at transition point B, which returns to transition point B in the flowchart 600, which continues at block 616 wherein a next current image edge is located in the gradient plot. If the edge strength of the rising edge does exceed the minimum edge strength, operations continue at block 704. The minimum edge threshold may be a constant threshold or dynamically changing threshold. The minimum edge threshold may change based on one or more of an amount of ambient light, operating condition of the laser, intensity of the line of coherent radiation, obstacles between the laser and end of the shaker screen which reduces intensity of the line of coherent radiation, and other reasons.

At block 704, a next current image edge is located in gradient plot. In particular, a rising edge of sufficient strength has been located. Now a falling edge of sufficient strength needs to be located (as further described below).

At block 706, a determination is made whether the next current image edge is rising or falling. If rising, operations continue at transition point B, which returns to transition point B in the flowchart 600, which continues at block 616 wherein a next current image edge is located in the gradient plot. If falling, operations of the flowchart 700 continue at block 708.

At block 708, a determination is made of whether an edge strength of the falling edge exceeds a minimum edge strength. If the edge strength of the falling edge does not exceed the minimum edge strength, operations return to block 704 where a next current image edge is located in gradient plot. If the edge strength of the falling edge does exceed the minimum edge strength, operations continue at block 710. The minimum edge strength may change based on one or more of an amount of ambient light, operating condition of the laser, intensity of the line of coherent radiation, obstacles between the laser and end of the shaker screen which reduces intensity of the line of coherent radiation, and other reasons. The minimum edge strength may be same as the minimum edge strength at block 702 or different.

At block 710, a determination is made whether a distance between the rising edge at block 702 and falling edge at 708 is substantially equal to a width threshold indicative of a width of the line of coherent radiation. If the distance is equal to the width threshold, then the image edge is associated with a line of coherent radiation. A line of coherent radiation is identified and operations may continue to block 712. If the distance is not equal to the width threshold, then the image edge is not associated with a line of coherent radiation and operations return to block 616.

At block 712, a distance is calculated between a position of the image edge on the shaker table and a baseline associated with the line of coherent radiation on the shaker table. The baseline may be a position of the line of coherent radiation on the shaker table if not deflected by the particle. The baseline may be determined as part of a calibration process when no particles are passing under the line of coherent radiation.

At block 714, one or more of a size and shape of the particle is identified is based on the distance determined in block 712. Additionally, a volume of a particle can be determined by multiplying a size of the particle by a velocity of the particle as the particle advances along the shaker screen. In one or more examples, a volume of a particle can be a volume per image. Operations continue at transition point B, which returns to transition point B in the flowchart 600, which continues at block 616 wherein a next current image edge is located in the gradient plot. Operations continue to cycle through blocks 616, 614, 702, 704, 706, 708, 710, 712, and 714 until the operations are stopped.

In one or more examples, color of one or more pixels associated with the image edge may also be compared to the color of the line of coherent radiation at block 714. The line of coherent radiation may be a certain color which is known based on the characteristics of the laser. Additionally, the pixels associated with the image edge may be a certain color. RGB components may represent the color. A difference in the color of the line of coherent radiation and color of the pixels is compared to a threshold level. If the difference is not beyond a threshold level, the processing continues to determine the size and shape the particle in block 714. For example, if each of RGB components associated with pixels and line of the coherent radiation does not exceed the threshold level, then the ambient light has not intruded. If the difference is beyond a threshold level, ambient light has intruded which makes edge detection as described below difficult. An alert may be raised as a result of the intrusion.

Figure 8:
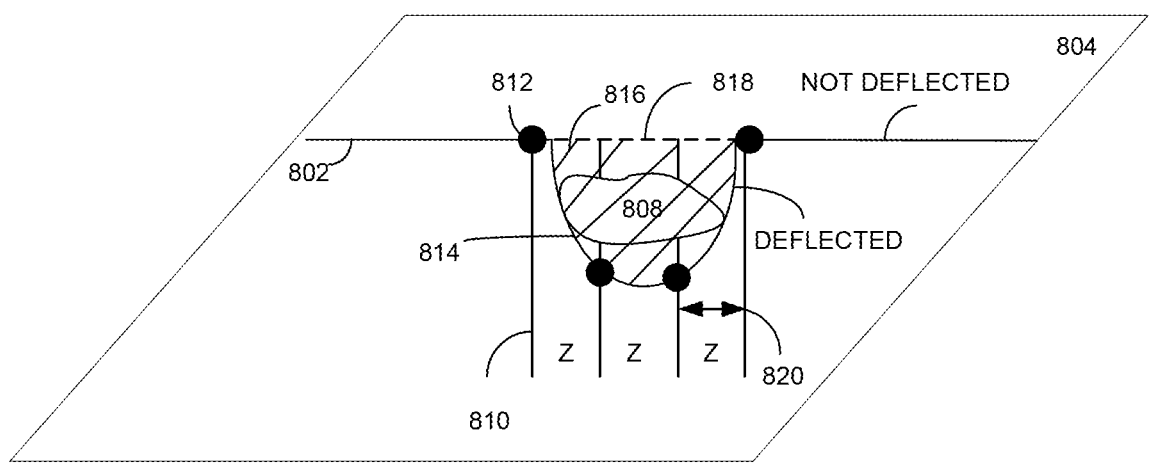
FIG. 8 illustrates determination of features of the downhole particles based on an example captured image and example gradient plot of edge strength.

FIG. 8 illustrates determination of features of the particles based on identification of the line of coherent radiation. A line of coherent radiation 802 is projected on a shaker screen 804. Some portions of the line of coherent radiation 802 may be deflected based on passing of a particle 808 on the shaker screen 804 under the line of coherent radiation 802 while other portions of the line of coherent radiation 802 are not deflected. The line of coherent radiation 802 may be divided into zones Z separated by lines 810 to facilitate determining the features of the particle 808. The zones may be a given size across as shown by arrow 820. For example, for a shaker table with a length of 48 inches, the zones may be uniformly 0.1 inches. In other examples, the zones may be non-uniformly sized. The line of coherent radiation 802 may intersect the lines 810 of the zones Z at points 812. In this regard, the size of each zone may be indicative of a resolution in identifying the features of the particles. If the line of coherent radiation does not intersect the vertical line 810, then the particle 808 is not detected. A curve 814 fit to the points indicates the shape of the particle. Further, an area 816 shown by the cross-hashing between the curve 814 and a baseline 818 indicates a size of the particle 808. The baseline 818 may indicate where the line of coherent radiation would be located if it was not deflected (shown as a dotted line). A position associated with the baseline on the shaker screen 804 may be determined during a calibration process when no particles on the shaker screen 804. The position may be further determined with and/or without ambient lighting. The process of determining shapes and sizes of particles may be repeated for various zones across the shaker screen 804. Volume of particle may be calculated by multiplying the area 816 by a velocity by which the particles are moving.

It should be understood that the apparatus and systems of various embodiments can be used in applications other than for drilling operations, and thus, various embodiments are not to be so limited. The illustrations of system 100 and systems 264 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules. Such apparatus and systems may further be included as sub-components within a variety of electronic systems, such as televisions, cellular telephones, personal computers, workstations, radios, video players, vehicles, signal processing for geothermal tools and smart transducer interface node telemetry systems, among others. Some embodiments include a number of methods.

Example Computer

Figure 9:
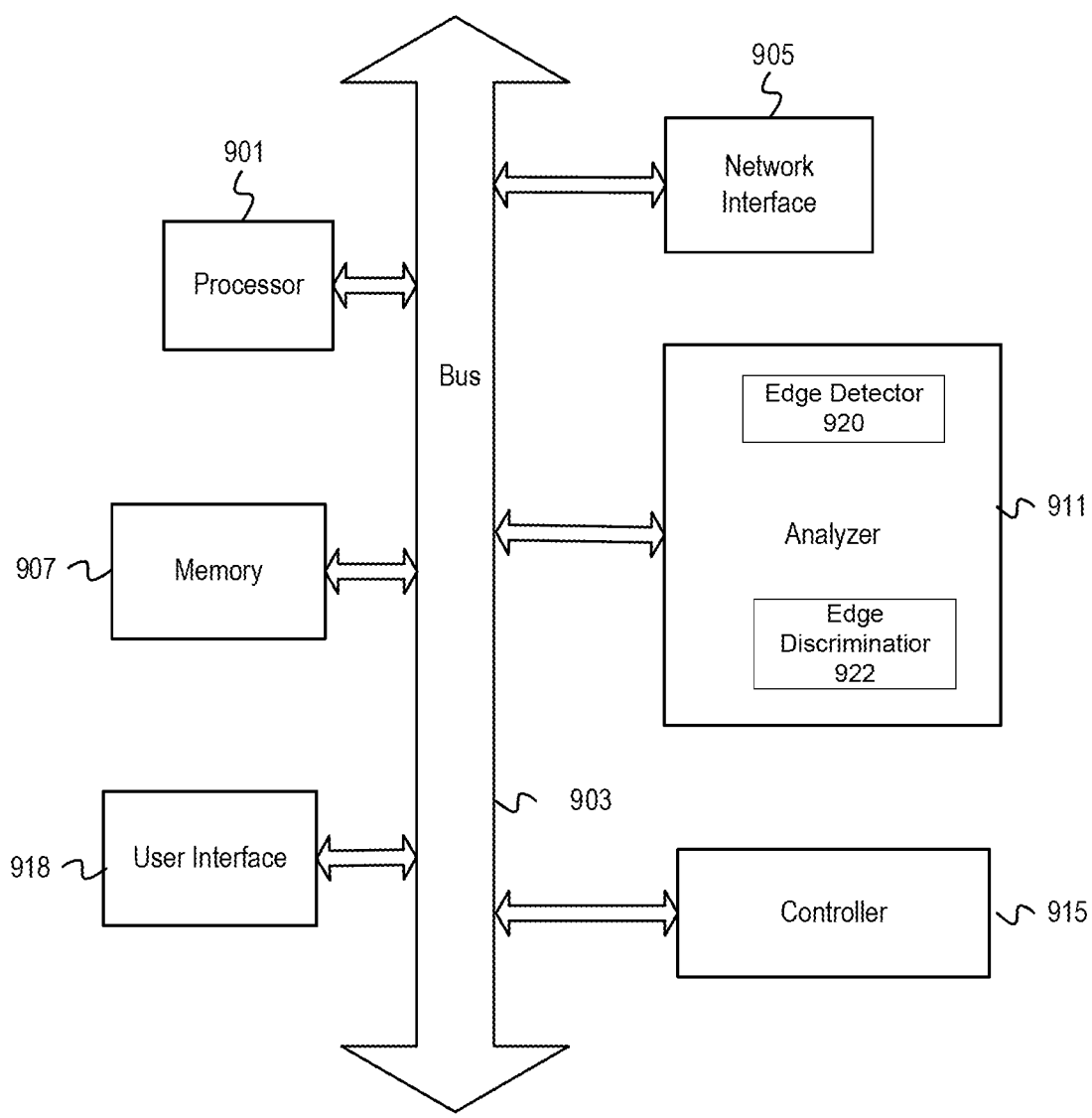
FIG. 9 is an example computer associated with identifying the line of coherent radiation in the captured image to facilitate the analysis of the downhole particles.

FIG. 9 depicts an example computer, according to one or more embodiments. The computer includes a processor 901 (possibly including multiple processors, multiple cores, multiple nodes, and/or implementing multi-threading, etc.). The computer includes memory 907. The memory 907 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more other possible realizations of non-transitory machine-readable media/medium.

The computer system also includes a bus 903 (e.g., PCI, ISA, PCI-Express etc.) and a network interface 905 (e.g., a Fiber Channel interface, an Ethernet interface, an internet small computer system interface, SONET interface, wireless interface, etc.).

The computer also includes an analyzer 911 and a controller 915. The analyzer 911 can perform processing and analyzing of the particles (as described above). The analyzer 911 may include an edge detector 920 for identifying image edges in a gradient plot and an edge discriminator 922 for discriminating image edges associated with noise and ambient light to facilitate identifying the line of coherent radiation in the gradient plot. The controller 915 can control the different operations that can occur in the response to results from the analysis. For example, the controller 915 can communicate instructions to the appropriate equipment, devices, etc. to alter the drilling and/or fracturing operations. In some cases, the controller 915 may be the same as the processor 901.

Any one of the previously described functionalities may be partially (or entirely) implemented in hardware and/or software (e.g., computer code, computer instructions, program instructions, program code) stored on a non-transitory machine readable medium/media. For example, the functionality may be implemented with an application specific integrated circuit, in logic implemented in the processor 901, in a co-processor on a peripheral device or card, etc. Further, realizations may include fewer or additional components not illustrated in FIG. 9 (e.g., video cards, audio cards, additional network interfaces, peripheral devices, etc.). The processor 901 and the memory 907 are coupled to the bus 903. Although illustrated as being coupled to the bus 903, the memory 907 may be coupled to the processor 901.

In one or more examples, the computer may further comprise a user interface 918. The user interface 918 may include a display such as a computer screen or other visual device and an input device such as a mouse, keyboard. The user input may be used to receive user input from engineering personnel associated with performing the size, volume, and shape measurement. For example, the user input may define the minimum edge strength and/or required distance between image edges in identifying the line of coherent radiation. The user interface 918 may also present various plots such as the gradient plots on a display screen for review by engineering personnel. The plots may be associated with identifying the line of coherent radiation and/or determining the size, volume, and shape of the particles.

The line of coherent radiation is illustrated above as a linear line. The line of coherent radiation may take other forms. For example, the line of coherent radiation may include segments of linear lines. Additionally, or alternatively, the line of coherent radiation may include segments of curved lines which may or may not be connected together. Still additionally, or alternatively, the line of coherent radiation may be a point. Characteristics of the line of coherent radiation determine the baseline described with respect to FIG. 8.

The above examples also describe a shaker screen having particles and on which the line of coherent radiation is projected. Generally, the particles and line of coherent radiation may be on a bed. The bed may be the shaker screen of the shaker, a discharge end of the shaker screen, or a bed downstream to the shaker. The one or more particles cross the line of coherent radiation by a transit such as a vibration of the bed, a plunger action, or linear motion of the bed. The vibration may be a one or more of a horizontal and vertical motion which causes the particles to move and cross the line of coherent radiation. The plunger action may be a vacuum action which pulls the particles to cross the line of coherent radiation. The linear motion may be a continuous movement of the bed which carries the particles under the line of coherent radiation.

It will be understood that each block of the flowchart illustrations and/or block diagrams, and combinations of blocks in the flowchart illustrations and/or block diagrams, can be implemented by program code. The program code may be provided to a processor of a general purpose computer, special purpose computer, or other programmable machine or apparatus.

As will be appreciated, aspects of the disclosure may be embodied as a system, method or program code/instructions stored in one or more machine-readable media. Accordingly, aspects may take the form of hardware, software (including firmware, resident software, program code, computer instructions, micro-code, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine readable medium(s) may be utilized. The machine-readable medium may be a machine-readable signal medium or a machine-readable storage medium. A machine-readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine-readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium may be any tangible medium that can contain, or store a program for use by or in connection with an instruction execution system, apparatus, or device. A machine-readable storage medium is not a machine-readable signal medium.

A machine-readable signal medium may include a propagated data signal with machine readable program code embodied therein, for example, in baseband or as part of a carrier wave. Such a propagated signal may take any of a variety of forms, including, but not limited to, electromagnetic, optical, or any suitable combination thereof. A machine-readable signal medium may be any machine-readable medium that is not a machine-readable storage medium and that can communicate, propagate, or transport a program for use by or in connection with an instruction execution system, apparatus, or device.

Program code embodied on a machine-readable medium may be transmitted using any appropriate medium, including but not limited to wireless, wireline, optical fiber cable, RF, etc., or any suitable combination of the foregoing.

Computer program code for carrying out operations for aspects of the disclosure may be written in any combination of one or more programming languages, including an object oriented programming language such as the Java® programming language, C++ or the like; a dynamic programming language such as Python; a scripting language such as Perl programming language or PowerShell script language; and conventional procedural programming languages, such as the "C" programming language or similar programming languages. The program code may execute entirely on a stand-alone machine, may execute in a distributed manner across multiple machines, and may execute on one machine while providing results and or accepting input on another machine.

The program code/instructions may also be stored in a machine-readable medium that can direct a machine to function in a particular manner, such that the instructions stored in the machine-readable medium produce an article of manufacture including instructions which implement the function/act specified in the flowchart and/or block diagram block or blocks.

Using the apparatus, systems, and methods disclosed herein may provide the ability to monitor changes in down hole particles (e.g., particles), so that the impact of drilling fluid properties and activities in the field can be assessed immediately. This ability may be used to increase efficiency by redirecting pumping and drilling operations in real-time, perhaps as part of a closed-loop control system.

While the aspects of the disclosure are described with reference to various implementations and exploitations, it will be understood that these aspects are illustrative and that the scope of the claims is not limited to them. In general, techniques for processing and analyzing of particles from downhole as described herein may be implemented with facilities consistent with any hardware system or hardware systems. Many variations, modifications, additions, and improvements are possible.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components. These and other variations, modifications, additions, and improvements may fall within the scope of the disclosure.

Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

Example Embodiments

Example embodiments include the following:

Embodiment 1 is a method, the method comprising: positioning a line of coherent radiation on a bed having one or more particles produced by a downhole operation in a borehole of a geologic formation; capturing an image of the bed, wherein one or more particles on the bed deflect the line of coherent radiation; detecting one or more image edges based on the captured image; and identifying the line of coherent radiation on the bed based on a pattern of the one or more image edges. Detecting one or more image edges as described in Embodiment 1 comprises determining a gradient plot associated with the captured image. The one or more image edges as described in any of the preceding embodiments includes a rising edge and falling edge; and wherein identifying the line of coherent radiation comprises locating the rising edge in the gradient plot, followed by the falling edge in the gradient plot, wherein the rising edge and falling edge are separated by a width of the line of coherent radiation. Any of the preceding embodiments further comprises comparing one or more of an edge strength of the rising edge and falling edge to a minimum edge strength value and determining that one or more of the rising edge and falling edge are not associated with the line of coherent radiation based on the comparison. The one or more particles as described in any of the preceding embodiments are illuminated by the line of coherent radiation and ambient light. Identifying the line of coherent radiation on the bed further as described in any of the preceding embodiments comprises comparing a color of the line of coherent radiation to a color of one or more pixels associated with the one or more image edges. The bed as described in any of the preceding embodiments is a shaker screen of a shaker, a discharge end of the shaker screen, or a bed downstream to the shaker and the one or more particles crosses the line of coherent radiation by one or more of a vibration of the surface, a plunger action, or linear motion of the bed. Any of the preceding embodiments further comprises determining a feature of the one or more particles based on the identification of the line of coherent radiation. Any of the preceding embodiments further comprises adjusting a drilling or fracturing operation based on the size, shape, or volume of the one or more particles.

Embodiment 2 is a system, the system comprising: a bed having one or more particles produced by a downhole operation in a borehole of a geologic formation; a laser which outputs a line of coherent radiation on the bed; an imaging device; a device to: position a line of coherent radiation on the bed having the one or more particles; capture, by the imaging device, an image of the bed, wherein one or more particles on the bed deflect the line of coherent radiation; detect one or more image edges based on the captured image; and identify the line of coherent radiation on the bed based on a pattern of the one or more image edges. The device to detect one or more image edges as described in Embodiment 2 comprises the device to determine a gradient plot associated with the captured image. The one or more image edges as described in any of the preceding embodiments of Embodiment 2 includes a rising edge and falling edge; and wherein the device to identify the line of coherent radiation comprises the device to locate the rising edge in the gradient plot, followed by the falling edge in the gradient plot, wherein the rising edge and falling edge are separated by a width of the line of coherent radiation. Any of the preceding embodiments of Embodiment 2 further comprises the device to compare one or more of an edge strength of the rising edge and falling edge to a minimum edge strength value and determine that the rising edge and falling edge are not associated with the line of coherent radiation based on the comparison. The one or more particles as described in any of the preceding embodiments of Embodiment 2 are illuminated by the line of coherent radiation and ambient light. Any of the preceding embodiments of Embodiment further comprises the device to compare a color of the line of coherent radiation to a color of one or more pixels associated with the one or more image edges. The bed as described in any of the preceding embodiments of Embodiment 2 is a shaker screen of a shaker, a discharge end of the shaker screen, or a bed downstream to the shaker and the one or more particles crosses the line of coherent radiation by one or more of a vibration of the surface, a plunger action, or linear motion of the bed. Any of the preceding embodiments of Embodiment 2 further comprises the device to determine a feature of the one or more particles based on the identification of the line of coherent radiation.

Embodiment 3 is one or more non-transitory machine-readable media comprising program code executable by a processor to: position a line of coherent radiation on a bed having one or more particles produced by a downhole operation in a borehole of a geologic formation; capture an image of the bed, wherein one or more particles on the bed deflect the line of coherent radiation; detect one or more image edges based on the captured image; and identify the line of coherent radiation on the bed based on a pattern of the one or more image edges. The program code to detect one or more image edges as described in Embodiment 3 comprises program code to determine a gradient plot associated with the captured image. The one or more image edges as described in any of the preceding embodiments of Embodiment 3 includes a rising edge and falling edge; and wherein the program code to identify the line of coherent radiation comprises program code to locate the rising edge in the gradient plot, followed by the falling edge in the gradient plot, wherein the rising edge and falling edge are separated by a width of the line of coherent radiation.

What is claimed is:

1. A method comprising:
   projecting a line of coherent radiation on a bed having one or more particles produced by a downhole operation in a borehole of a geologic formation;
   capturing an image of the bed, wherein one or more particles on the bed deflect the line of coherent radiation; and
   detecting one or more image edges based on the captured image wherein detecting the one or more image edges comprises detecting a positive interval in a change in intensity of the captured image followed by a negative interval in the change in intensity of the captured image,
   wherein the bed comprises at least one of a shaker screen of a shaker, a discharge end of the shaker screen, and a bed downstream to the shaker, and wherein the one or more particles crosses the line of coherent radiation by a transit.

2. The method of claim 1, wherein the one or more particles are illuminated by the line of coherent radiation and ambient light.

3. The method of claim 1, further comprising determining at least one of a feature, a size, a shape, and a volume of the one or more particles based on the one or more image edges detected.

4. The method of claim 3, further comprising adjusting at least one of a drilling and a fracturing operation based on at least one of the feature, the size, the shape, or the volume of the one or more particles.

5. The method of claim 1, wherein detecting a positive interval of a change in intensity of the captured image comprises detecting a positive interval in a gradient of the captured image and wherein detecting a negative interval in the change in intensity of the captured image comprises detecting a negative interval in the gradient of the captured image.

6. The method of claim 5, wherein detecting one or more image edges comprises determining the gradient associated with the captured image, and
   wherein at least a subset of the one or more image edges are edges associated with the one or more particles in the captured image.

7. The method of claim 5, wherein detecting the one or more image edges comprises detecting that an end of the positive interval in the gradient and a beginning of the negative interval in the gradient are separated by a width of the line of coherent radiation.

8. The method of claim 5, wherein detecting the one or more image edges comprises:
   detecting that an absolute value of a magnitude of a peak of the positive interval exceeds a minimum positive interval edge strength threshold value; and
   detecting that an absolute value of a magnitude of a peak of the negative interval exceeds a minimum negative interval edge strength threshold value.

9. The method of claim 1, wherein detecting at least one of the positive interval and the negative interval of the change in intensity of the captured image comprises detecting the change in intensity of the captured image in a color of the line of coherent radiation.

10. A system comprising:
a bed having one or more particles produced by a downhole operation in a borehole of a geologic formation, wherein the bed comprises at least one of a shaker screen of a shaker, a discharge end of the shaker screen, and a bed downstream to the shaker, and wherein the one or more particles crosses the line of coherent radiation by a transit;
a laser configured to project a line of coherent radiation on the bed;
an imaging device configured to capture an image of the bed having the one or more particles; and
a device to:
detect one or more image edges based on the image captured by the imaging device, wherein the one or more image edges comprise a positive interval in a change in intensity of the captured image followed by a negative interval in the change in intensity of the captured image.

11. The system of claim 10, wherein the device to detect one or more image edges comprises the device to determine a gradient associated with the captured image,
wherein a positive interval of a change in intensity of the captured image comprises a positive interval in a gradient of the captured image and wherein a negative interval of the change in intensity of the captured image comprises a negative interval in the gradient of the captured image, and
wherein at least a subset of the one or more image edges are edges associated with the one or more particles of the captured image.

12. The system of claim 11, wherein the device to detect one or more image edges further comprises the device detect one or more image edges wherein the positive interval in the gradient and the negative interval in the gradient are separated by a width of the line of coherent radiation.

13. The system of claim 11, further comprising the device to
detect that an absolute value of a magnitude of the gradient maximum of the positive interval exceeds a minimum positive interval edge strength threshold value; and
detect that an absolute value of a magnitude of the gradient minimum of the negative interval exceeds a minimum negative interval edge strength threshold value.

14. The system of claim 10, wherein the one or more particles are illuminated by the line of coherent radiation and ambient light.

15. The system of claim 10, wherein the device to detect one or more image edges based on the captured image further comprises the device to detect one or more image edges based on a change in intensity of the captured image in a color of the line of coherent radiation.

16. The system of claim 10, further comprising the device to determine a feature of the one or more particles based on the one or more image edges detected.

17. One or more non-transitory machine-readable media comprising program code executable by a processor to operate a system configured to:
project a line of coherent radiation on a bed having one or more particles produced by a downhole operation in a borehole of a geologic formation;
capture an image of the bed; and
detect one or more image edges based on the captured image, wherein the one or more image edges comprise a positive interval in a change in intensity of the captured image followed by a negative interval in the change in intensity of the captured image,
wherein the bed comprises at least one of a shaker screen of a shaker, a discharge end of the shaker screen, and a bed downstream to the shaker, and wherein the one or more particles crosses the line of coherent radiation by a transit.

18. The one or more non-transitory machine-readable media of claim 17, wherein the program code to detect the one or more image edges comprises program code to locate the positive interval in the change in intensity and the negative interval in the change in separated by a width of the line of coherent radiation.

* * * * *